(12) United States Patent
Harrah et al.

(10) Patent No.: US 12,023,004 B2
(45) Date of Patent: Jul. 2, 2024

(54) ATTACHMENT FOR AN IMAGING DEVICE

(71) Applicant: Boston Scientific Scimed, Inc., Maple Grove, MN (US)

(72) Inventors: Timothy P. Harrah, Cambridge, MA (US); Christopher L. Oskin, Grafton, MA (US); Derrick Lenz, Pompton Plains, NJ (US); Arpita Banerjee, Bangalore (IN); Pavan Misra, Bangalore (IN); Abhijit Takale, Pune (IN); Sandesh Gavade, Bangalore (IN)

(73) Assignee: Boston Scientific Scimed, Inc., Maple Grove, MN (US)

( * ) Notice: Subject to any disclaimer, the term of this patent is extended or adjusted under 35 U.S.C. 154(b) by 3 days.

(21) Appl. No.: 17/659,893

(22) Filed: Apr. 20, 2022

(65) Prior Publication Data
US 2022/0240761 A1 Aug. 4, 2022

Related U.S. Application Data

(63) Continuation of application No. 15/416,071, filed on Jan. 26, 2017, now Pat. No. 11,330,966.

(60) Provisional application No. 62/288,707, filed on Jan. 29, 2016.

(51) Int. Cl.
*A61B 1/00* (2006.01)
*A61B 1/018* (2006.01)
*A61B 1/307* (2006.01)

(52) U.S. Cl.
CPC ...... *A61B 1/00135* (2013.01); *A61B 1/00073* (2013.01); *A61B 1/00105* (2013.01); *A61B 1/00117* (2013.01); *A61B 1/00128* (2013.01); *A61B 1/018* (2013.01); *A61B 1/307* (2013.01)

(58) Field of Classification Search
CPC ............ A61B 1/00142; A61B 1/00135; A61B 1/00137; A61B 1/00154; A61B 1/31; A61B 1/267–2676; A61B 1/00121
See application file for complete search history.

(56) References Cited

U.S. PATENT DOCUMENTS

| | | |
|---|---|---|
| 4,132,227 A | 1/1979 | Ibe |
| 5,048,508 A | 9/1991 | Storz |
| 5,169,397 A | 12/1992 | Sakashita et al. |
| 5,645,519 A | 7/1997 | Lee et al. |
| 6,174,280 B1 | 1/2001 | Oneda et al. |
| 6,994,667 B2 | 2/2006 | Singh |

(Continued)

FOREIGN PATENT DOCUMENTS

| | | |
|---|---|---|
| DE | 3834156 A1 | 4/1990 |
| WO | 2015098210 A1 | 7/2015 |
| WO | 2016054202 A1 | 4/2016 |

OTHER PUBLICATIONS

International Search Report and Written Opinion for International Application No. PCT/US2017/015051 dated Apr. 25, 2017 (15 pages).

*Primary Examiner* — Alexandra L Newton
(74) *Attorney, Agent, or Firm* — Bookoff McAndrews PLLC

(57) ABSTRACT

An attachment for an imaging device may include a first sheath including a proximal end, a distal end, and a lumen extending between the proximal end and the distal end; a second sheath positioned around an exterior of the first sheath; and a connector coupled to the first sheath and configured to be coupled to the imaging device.

18 Claims, 9 Drawing Sheets

(56) References Cited

U.S. PATENT DOCUMENTS

| | | |
|---|---|---|
| 9,687,273 B2 | 6/2017 | Henzler et al. |
| 2005/0277811 A1 | 12/2005 | Richards et al. |
| 2006/0221465 A1 | 10/2006 | Noguchi et al. |
| 2007/0088247 A1* | 4/2007 | Bliweis .............. A61B 1/00154 606/21 |
| 2008/0071269 A1* | 3/2008 | Hilario ............... A61B 1/00154 606/50 |
| 2009/0143648 A1 | 6/2009 | Sutoh et al. |
| 2010/0280318 A1 | 11/2010 | Chang |
| 2012/0010646 A1 | 1/2012 | Keith et al. |
| 2013/0345515 A1 | 12/2013 | Fitzmaurice |
| 2014/0024896 A1 | 1/2014 | West |
| 2014/0114126 A1* | 4/2014 | Dresher ............... A61B 1/0125 600/106 |
| 2016/0073861 A1 | 3/2016 | Kaneko |
| 2018/0289394 A1* | 10/2018 | Shah .............. A61B 17/320016 |

\* cited by examiner

ATTACHMENT FOR AN IMAGING DEVICE

CROSS-REFERENCE TO RELATED APPLICATION(S)

This application claims the benefit of priority under 35 U.S.C. § 119 to U.S. application Ser. No. 15/416,071, filed on Jan. 26, 2017, which claims benefit to U.S. Provisional Patent Application No. 62/288,707, filed Jan. 29, 2016, the entirety of each of which is incorporated herein by reference.

TECHNICAL FIELD

Embodiments of the present disclosure relate generally to medical devices for providing an access pathway through a patient's urinary tract.

BACKGROUND

A ureteroscopy is an examination of the ureter or kidney of a patient using a ureteroscope. Ureteroscopes typically include a long, thin, flexible portion that can be inserted through the patient's urethra, bladder, and ureteral orifice connecting the bladder and the ureter. Ureteroscopes typically further include a camera and lighting system to adequately visualize the scope's pathway and the working area within the ureter or kidney. Often, a ureteroscopy procedure involves treating a stone that has lodged in the patient's mid to upper ureter or within a calyx of the kidney.

Currently, before a ureteroscope can be inserted into a patient's ureter, a separate device called a cystoscope is required to pass through the urethra, examine the bladder, and find the ureteral orifice. An examination of the bladder is called a cystoscopy. The cystoscope includes a separate camera and lighting system, is often shorter than a ureteroscope, and is typically more rigid than a ureteroscope. Once the ureteral orifice has been located by the cystoscope, a guidewire is inserted into the ureter. The cystoscope is then removed from the patient, leaving the guidewire in place. An access sheath is often then inserted over the guidewire through the urethra, bladder, and into the ureter. The guidewire is removed and the ureteroscope can then be inserted through the access sheath and into the ureter.

The use of two different scopes and accompanying equipment during a ureteroscopy is expensive. Furthermore, the additional steps required to insert and remove the cystoscope from the patient and subsequently insert the ureteroscope through the urethra, bladder, and ureter increases the length of the procedure.

SUMMARY

Examples of the present disclosure relate to, among other things, one or more sheaths for an imaging device, a connector for connecting the sheath and the imaging device, and methods for using the sheath and connector with the imaging device. Each of the examples disclosed herein may include one or more of the features described in connection with any of the other disclosed examples.

In one example, an attachment for an imaging device may include a first sheath including a proximal end, a distal end, and a lumen extending between the proximal end and the distal end; a second sheath positioned around an exterior of the first sheath; and a connector coupled to the first sheath and configured to be coupled to the imaging device.

Additionally or alternatively, any of the attachments described herein may include one or more of the following features: the first sheath may include a proximal portion having a larger diameter than a distal portion of the first sheath; the lumen may be a first lumen, and the first sheath may further include a second lumen; the second sheath may include a proximal end, a distal end, and an opening in a wall of the second sheath, wherein the opening extends from the proximal end of the second sheath to the distal end of the second sheath; the second sheath may have a length that is less than a length of the first sheath; the connector may be removably coupled to the first sheath; and the connector may include an elongated body with an interior configured to receive a portion of the imaging device, and on an interior wall, at least one of a liner or a rib, wherein the at least one of the liner or the rib is configured to secure the imaging device relative to the connector.

In another example, an attachment for an imaging device may include a first sheath including a proximal end, a distal end, and a lumen extending between the proximal end and the distal end; a second sheath; and a connector coupled to the first sheath, wherein the connector includes an interior configured to receive a portion of the imaging device.

Additionally or alternatively, any of the attachments described herein may include one or more of the following features: the proximal end of the first sheath may have a larger diameter than the distal end of the first sheath; the second sheath may be positioned around an exterior of the first sheath; the second sheath may be secured to the first sheath by a friction fit, and the second sheath may be removably coupled to the first sheath; the connector may include an opening in a side wall adjacent to a distal end of the connector, wherein the opening is configured to receive a tubular member of the imaging device; the connector may be removably coupled to the proximal end of the first sheath; the connector may include a plurality of ribs protruding from an interior wall of the connector; and the connector may include a silicone liner on an interior wall of the connector.

In one example, a method for using an attachment for an imaging device includes inserting a distal end of a tubular member of the imaging device, a distal end of a first sheath, and a distal end of a second sheath through a urethra of a patient and into a bladder of the patient, wherein the second sheath is positioned around an exterior of the first sheath; removing the second sheath from the patient; inserting the distal end of the tubular member and the distal end of the first sheath into a ureter of the patient; and moving the distal end of the tubular member relative to the first sheath.

Additionally or alternatively, any method described herein may include one or more of the following features or steps: the method may further include inserting at least a portion of the tubular member of the imaging device into the lumen of the first sheath and fixing the first sheath relative to the imaging device; fixing the first sheath relative to the imaging device may include coupling a connector to the imaging device and coupling the connector to the first sheath; the method may further include decoupling the connector from the first sheath; and the method may further include moving the distal end of the tubular member into a kidney of the patient.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate aspects of the present disclosure and together with the description, serve to explain the principles of the disclosure.

DETAILED DESCRIPTION

Examples of the present disclosure may include attachments for coupling to an imaging device. The attachment may include one or more sheaths and a connector for coupling the one or more sheaths to the imaging device. The imaging device may be a ureteroscope or any other device with an imaging system for viewing an interior of a patient. In certain examples, a second sheath may be positioned around a distal portion of a first sheath, and the first sheath may be coupled to the connector. In some examples, the attachment may allow a medical practitioner to perform both a cystoscopy procedure and a ureteroscopy procedure using the same camera, lighting, and other equipment. The related methods disclosed in this application may allow a medical practitioner to eliminate certain steps typically associated with ureteroscopy procedures.

The terms "proximal" and "distal" are used herein to refer to the relative positions of the components of exemplary medical devices. When used herein, "proximal" refers to a position relatively closer to a user of a medical device. In contrast, "distal" refers to a position relatively farther away from the user of a medical device.

Figure 1:
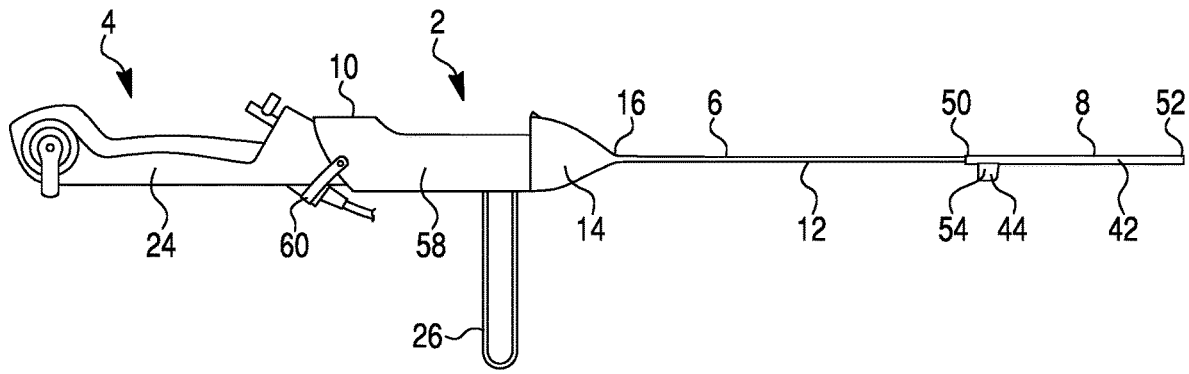
FIG. 1 illustrates an imaging device and an attachment that includes a connector, a first sheath, and a second sheath, according to a first example.

FIG. 1 illustrates an attachment 2 according to a first example. The attachment 2 may be coupled to an imaging device 4. Among other features, the attachment 2 may include a first sheath 6, a second sheath 8, and a connector 10.

The first sheath 6 may extend from a proximal end to a distal end and may include a proximal portion 14 and an elongated shaft 12. The first sheath 6 may have a length of between 200-700 mm, 250-650 mm, 300-600 mm, or 350-550 mm. If being used for a child, the first 6 sheath may have a length less than 200 mm. The elongated shaft 12 and the proximal portion 14 may be formed as a single component or may be two separate components permanently or removably coupled together. The elongated shaft 12 may extend from a proximal end 16 adjacent the proximal portion 14 to a distal end 18 (see FIG. 2). The exterior of shaft 12 may have a diameter of between 1-8 mm, 2-7 mm, 3-6 mm, or 4-5 mm. The proximal portion 14 may expand radially outward relative to the elongated shaft 12 and may have a larger diameter than the elongated shaft 12. The first sheath 6 may include any appropriate biocompatible material, such as polymers, urethane, fluorine-polymer blend, or metals (e.g., stainless steel).

Figure 2:
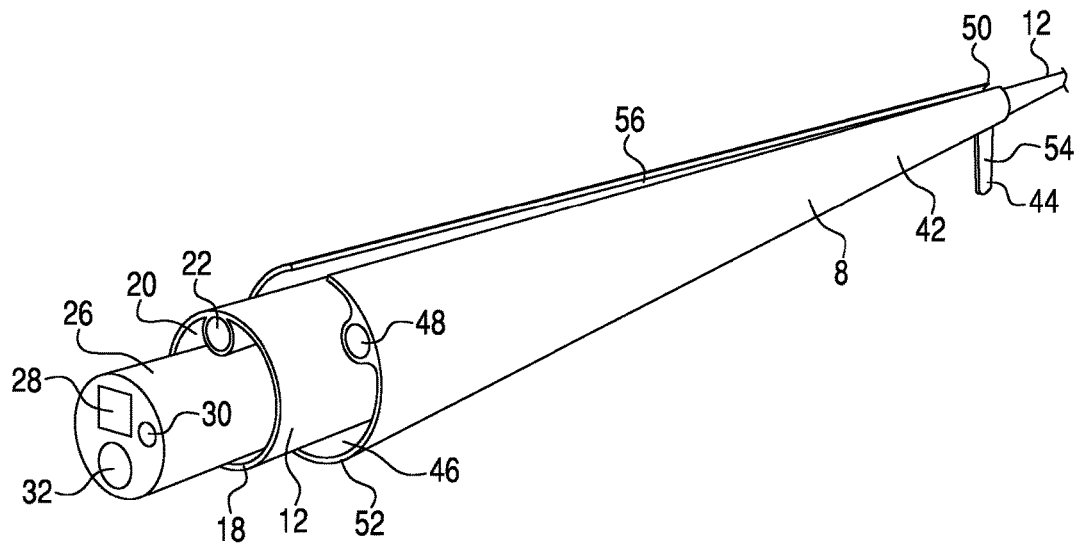
FIG. 2 illustrates a perspective view of a distal end of the first sheath and the second sheath of FIG. 1, with a tubular member of the imaging device within a lumen of the first sheath.

Referring to FIG. 2, the shaft 12 may include a main lumen 20 and a side lumen 22. The main lumen 20 may be configured to receive a tubular member 26 of an imaging device 4, described further below. The side lumen 22 may be configured to receive a guidewire. In other examples, the first sheath 6 does not include a separate side lumen 22, or the first sheath 6 includes two or more side lumens 22. The first sheath 6 may further include one or more entry ports on the proximal portion 14 to receive one or more guidewires. The entry ports may lead to the main lumen 20 of the first sheath 6 or to the side lumen 22 of the first sheath 6.

Figure 4:
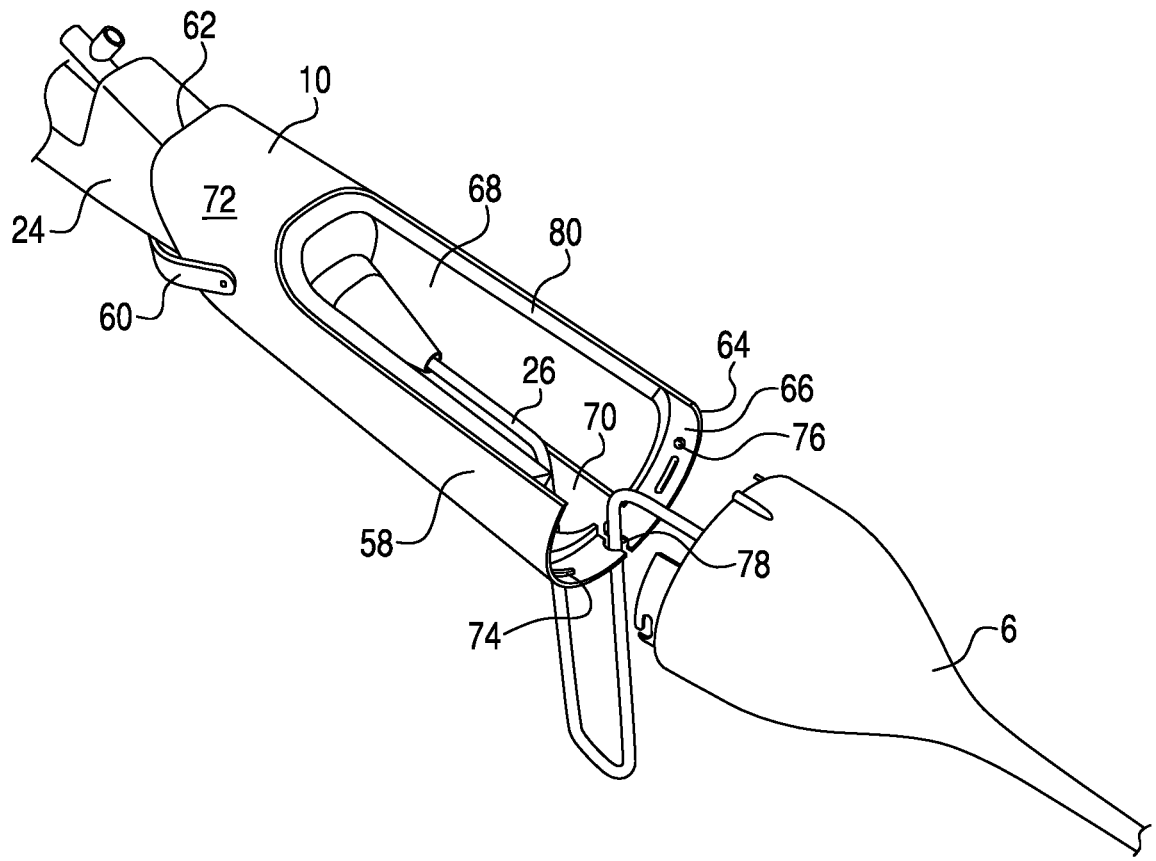
FIG. 4 illustrates the connector and first sheath of FIG. 1 separated from each other.

Referring to FIGS. 1 and 2, an imaging device 4 for use with the attachment 2 may be a ureteroscope or any other device with a camera system. The imaging device 4 may include a handle assembly 24 and a tubular member 26. The proximal end of the tubular member 26 may be connected to the handle assembly 24, as shown in FIG. 4. A distal portion of the tubular member 26 may be positioned within the main lumen 20 of the shaft 12. The imaging device 4 may further include a variety of other components necessary for viewing the interior of a body, such as camera and lighting equipment. As shown in FIG. 2, a camera 28 and a light 30 may be located at the distal end of the tubular member 26. Optical fiber cables may be used to transmit light from the proximal end of tubular member 26 to the distal end of tubular member 26. The camera may be coupled to the distal end of the tubular member 26, with power and signal wires extending proximal to the ureteroscope handle 24. The tubular member 26 may include one or more working lumens 32 for tools and irrigation. Working lumen 32 or separate channels in the tubular member 26 may hold the wires and/or fibers connecting the camera 28 and light 30 to a power source, LED, and/or other processing and control equipment, along with mechanical cables to permit maneuverability of the tubular member 26.

Figure 5:
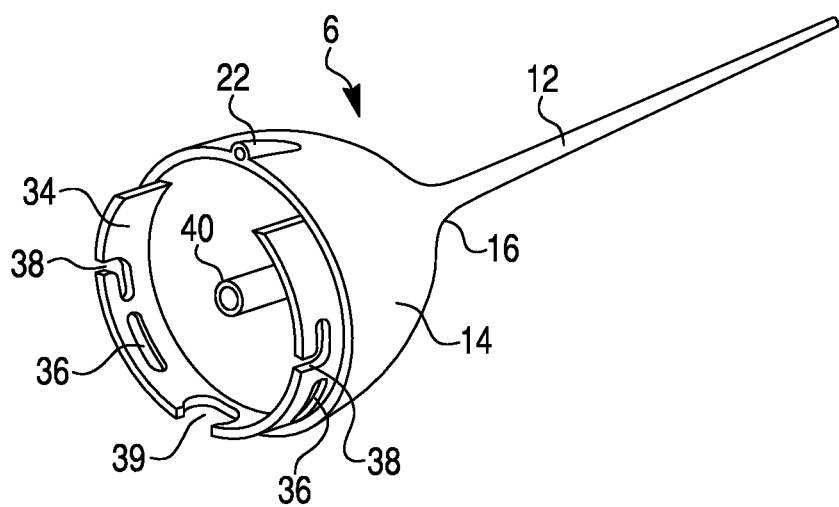
FIG. 5 illustrates a proximal view of the first sheath.

Referring to FIGS. 1 and 5, the inner and/or the outer wall of the proximal portion 14 of the first sheath 6 may expand radially outward and in a proximal direction from the proximal end 16 of the shaft 12. In other words, the proximal portion 14 may generally form a funnel shape. The inner and/or outer wall of the proximal portion 14 may be curved. The proximal portion 14 may include a lip 34 at its proximal end. The lip 34 may facilitate connection to the connector 10 in a manner described in more detail below. The lip 34 may include one or more slots 36. The slots 36 may include an elongated shape and may extend partially or fully through the material of lip 34. The slots 36 may receive corresponding protrusions located on the connector 10. The lip may further include one or more slots 38. The slots 38 may similarly extend partially or fully through the material of lip 34 and may receive corresponding protrusions located on the connector 10. The slots 38 may include a bend to facilitate a secure attachment of the sheath 6 to the connector 10. The lip may further include an opening 39, which may extend through the lip 34. The opening 39 may include a generally round shape and may be configured to receive the tubular member 26 of the imaging device 4.

The first sheath 6 may include a port 40 for receiving a tubular member 26 of an imaging device 4. The port 40 may include a lumen and may be a proximal extension of the elongated shaft 12. The port 40 may be located within the proximal portion 14 and may be centered within the proximal portion 14. The port 40 may facilitate secure positioning of the tubular member 26 within the first sheath 6.

According to another example, the first sheath 6 does not include a port 40. Instead, the inner wall of the proximal portion 14 may serve as a guide for insertion of a tubular member 26 into the shaft 12. For example, to place the tubular member 26 within the main lumen 20 of the shaft 12, a distal end of the tubular member 26 may be inserted into the space within proximal portion 14, and the inner walls of the proximal portion 14 may guide the distal end of the tubular member 26 towards the proximal end 16 of the shaft 12.

Referring to FIG. 5, the proximal portion 14 of the shaft 6 may include a proximal portion of guidewire lumen 22. Guidewire lumen 22 may travel from the inlet shown on the proximal portion 14 of the shaft 6 (FIG. 5), within the wall of proximal portion 14, and down the length of the shaft 12 to the exit at the distal end 18 of the shaft 12 (FIG. 2).

Referring to FIGS. 1 and 2, the attachment 2 may further include a second sheath 8. The second sheath 8 may include an elongated shaft 42, a grip 44, a main lumen 46, and a side lumen 48.

The elongated shaft 42 of the second sheath 8 may extend from a proximal end 50 to a distal end 52. The elongated shaft 42 may have a length of between 50-350 mm, 100-300 mm, or 150-250 mm. If being used for a child, the second sheath 8 may have a length less than 50 mm. The second sheath 8 may have a length that is less than the length of the first sheath 6. The exterior of shaft 42 may have a diameter of between 2-10 mm, 3-9 mm, 4-8 mm, or 5-7 mm. The shaft 42 of the second sheath 8 may be dimensioned to fit radially outward from and coaxial with the elongated shaft 12 of the first sheath 6 (e.g., the elongated shaft 12 of the first sheath 6 may fit within the main lumen 46 of the second sheath 8). Additionally or alternatively, the second sheath 8 may be positioned around an exterior of the first sheath 6. The shaft 42 may include any appropriate biocompatible material, such as polymers, urethane, fluorine-polymer blend, or metals (e.g., stainless steel). Referring to FIG. 2, the shaft 42 of the second sheath 8 may include a main lumen 46 and a side lumen 48. As described above, the main lumen 46 may be configured to receive the elongated shaft 12 of the first sheath 6. The side lumen 48 may be configured to receive a guidewire. In an alternative example, the second sheath 8 does not include a separate side lumen 48.

The second sheath 8 may include a grip 44. The grip 44 may be a protrusion from the elongated shaft 42. As shown in the side view of FIG. 1, the grip 44 may include a first gripping face 54 having a substantially rectangular shape and a second gripping face (not shown) on the opposite side. As shown in FIG. 2, the thickness of the grip 44, as viewed looking in a proximal direction from the distal end 52 of the shaft 42, may be the grip's smallest dimension. To control the position of the second sheath 8, a user may place fingers on the first gripping face 54 and the second gripping face opposite the first face 54. Alternatively, the grip 44 may include first and second gripping faces having any other shape, such as square, circular, ovular, or irregular shapes, or the gripping faces of the grip 44 may be positioned to face the proximal and distal ends of the second sheath 8, instead of facing the sides. Additionally or alternatively, the grip 44 may include a loop, rod, or other structure to facilitate grasping by a user.

Referring to FIG. 2, the shaft 42 of the second sheath 8 may include an opening 56 extending from the proximal end 50 to the distal end 52 of the shaft 42. The opening may permit the second sheath 8 to be pulled away from the first sheath 6 without having to withdraw the first sheath 6 proximally relative to the second sheath 8. For example, the second sheath 8 may be pulled by the grip 44 away from the elongated shaft 12 of the first sheath 6 until the elongated shaft 12 exits the lumen 46 of the second sheath 8 through the opening 56 (see FIG. 10, to be described further below). The material of the second sheath 8 may have sufficient flexibility to allow the material on either side of opening 56 to spread apart, allowing the opening 56 to widen to accommodate the width of elongated shaft 12.

The relationship between the first sheath 6, second sheath 8, and tubular member 26 of an imaging device 4 can be seen in FIG. 2, which illustrates a perspective view of the distal ends of each of these three components. The elongated shaft 12 of the first sheath 6 may be positioned within the main lumen 46 of the elongated shaft 42 of the second sheath 8. The first sheath 6 may be held in place relative to the second sheath 8 by a friction fit. However, if a user applies force, the friction forces may be overcome and the first sheath 6 or the second sheath 8 may be movable in proximal and distal directions relative to the other sheath. The tubular member 26 may be positioned within the main lumen 20 of the elongated shaft 12 of the first sheath 6. If not fixed in place, the tubular member 26 may be movable in proximal and distal directions relative to the first sheath 6.

Referring back to FIG. 1, the attachment 2 may further include a connector 10. The connector 10 may fix the first and second sheaths 6, 8 relative to the imaging device 4. The connector 10 may be removably coupled to the first sheath 6. Alternatively, the connector 10 may be integrally formed with the first sheath 6.

Figure 3:
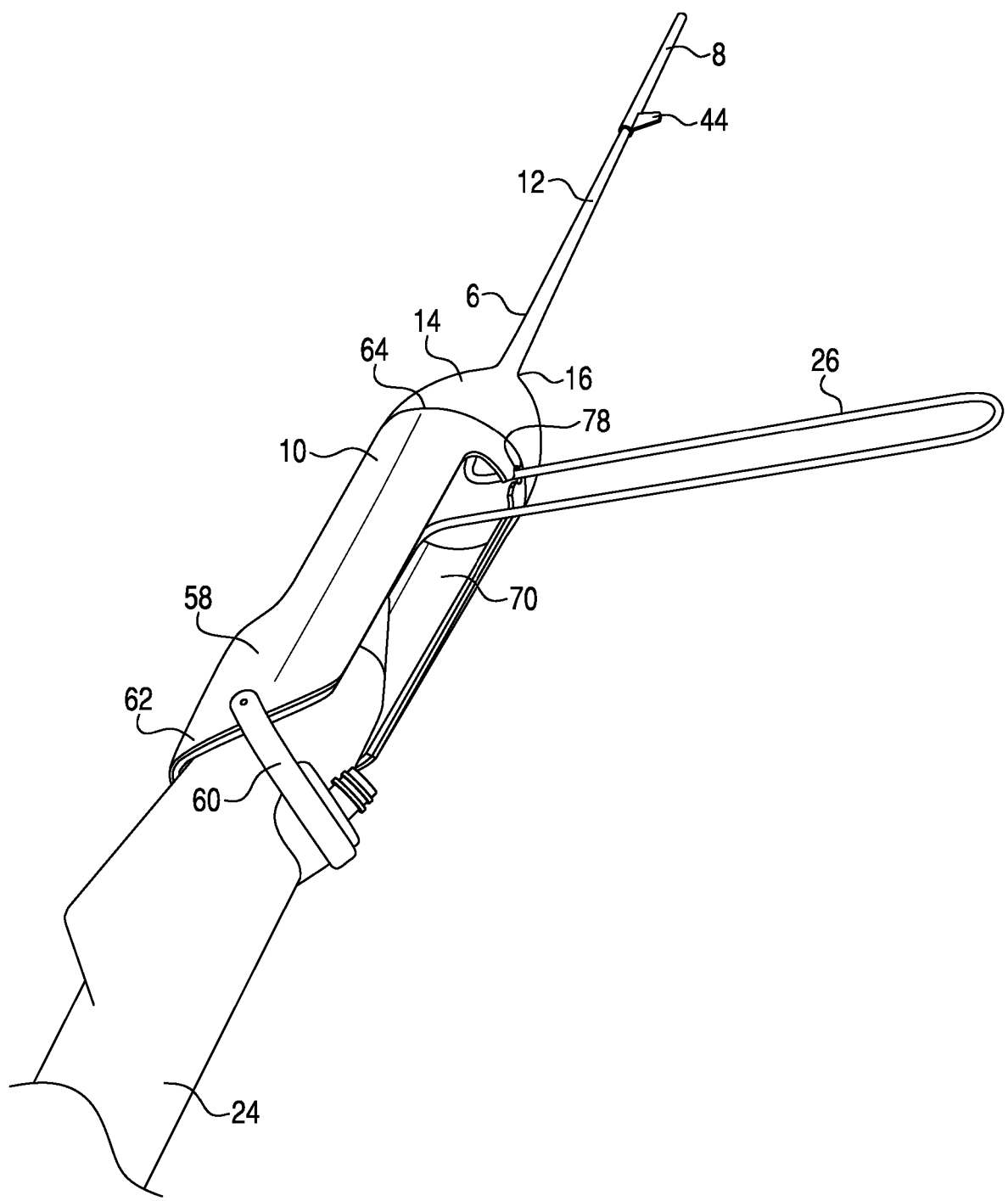
FIG. 3 illustrates a bottom perspective view of the components of FIG. 1.

Referring to FIGS. 1, 3 and 4, the connector 10 may include a body portion 58 having one or more openings 68, 70. The body portion 58 may extend from a proximal end 62 to a distal end 64 and may define a hollow interior configured to receive components of the imaging device 4. The body portion 58 may have a length of between 90-170 mm, 100-160 mm, 110-150 mm or 120-140 mm. The interior of the proximal portion of the body portion 58 may be shaped to fit securely around the exterior of the imaging device 4, such as the LithoVue scope developed by Boston Scientific Corp. For example, the interior of a proximal region 72 of the connector 10 may include a relatively flat upper surface to rest on an upper surface of the imaging device 4, and two curved surfaces to rest against the sides of the imaging device 4.

The walls of the connector 10 may include the first opening 68 and the second opening 70. The first opening 68 may be formed in an upper wall of the connector 10 and may extend along a portion of the length of connector 10. The first opening 68 may extend from a location adjacent the proximal region 72 to the distal end 64 of the connector 10. The opening 68 may therefore form a U-shape, with the ends of the U positioned at the distal end 64 of the connector 10. The first opening 68 may allow the user to adjust the placement of the tubular member 26, a portion of which may be positioned within the interior of connector 10.

The second opening 70 may be formed in a lower wall of the connector 10. The second opening 70 may generally extend from the proximal end 62 to the distal end 64 of the connector 10, as shown in FIG. 3. Near the distal end 64, the second opening 70 may be connected to a smaller opening 78 configured to receive the tubular member 26 of the imaging device 4. The tubular member 26 may be able to pass from the second opening 70 to the smaller opening 78 through a passage connecting the two openings. The second opening 70 may provide the connector 10 with flexibility to fit around different models of imaging devices. For example, the width of the second opening 70 may expand to allow the connector 10 to fit around larger imaging devices. The second opening 70 may also allow the tubular member 26 of the imaging device 4 to extend below the connector 10, as shown in FIG. 3. Finally, the second opening 70 may simplify detachment of the connector 10 from the imaging device 4 by allowing the connector 10 to be pulled away from the imaging device 4, with the imaging device 4 passing through opening 70.

Referring to FIG. 4, a lip 66 may be positioned at the distal end 64 of the connector 10. The lip 66 may be an extension of the body portion 58 of the connector 10 and may be configured to mate with the lip 34 of the first sheath 6. The lip 66 may include one or more protrusions 74 configured to mate with slots 36 of the first sheath 6 and one or more protrusions 76 configured to mate with the slots 38 of sheath 6. In another aspect, the lip 66 of the connector 10 may include slots and the lip 34 of the first sheath may include protrusions, or each lip may include a combination of slots and protrusions to facilitate coupling of the two components. As noted above, the lip 66 may further include an opening 78 configured to receive the tubular member 26 of imaging device 4. The opening 78 of the lip 66 in combination with the opening 39 of the first sheath 6 may secure the tubular member 26 with respect to the attachment 2, which may be useful during medical procedures. The connector 10 and the first sheath 6 may be removably coupled to each other in a manner described further below.

The connector 10 may include features to secure the connector 10 to the imaging device 4. For example, the connector 10 may include a strap 60 that connects to each side of the body portion 58 and extends across the second opening 70 and around the bottom of the imaging device 4. The strap 60 may wrap over a port protrusion on the bottom of the imaging device 4, as shown in FIG. 3. Strap 60 may be an appropriate length to securely hold the imaging device 4 within the interior of the connector 10. Strap 60 may removably connect to one or both sides of the body portion 58 by a snap, a protrusion on one component and an opening on the other, a magnet, or any other appropriate fastening mechanism. The strap 60 may include any appropriate material, such as silicone rubber or polymers.

The connector 10 may further include a lining 80 that may help secure the imaging device 4 within the connector 10. The lining 80 may include a material that has a tendency to return to its original shape after being compressed. For example, the lining 80 may include a material that can be compressed by an imaging device placed within the connector 10 such that pressure is then exerted on the imaging device by the lining 80. The lining 80 may include silicone. The lining 80 may extend along all or a portion of the interior of the connector 10 and may be present in areas that contact an imaging device 4, such as the interior of proximal region 72. The lining 80 may have a thickness of between 1-10 mm, 2-7 mm, 2-6 mm, 2-4 mm, 3-5 mm, or 3-4 mm.

Figure 6:
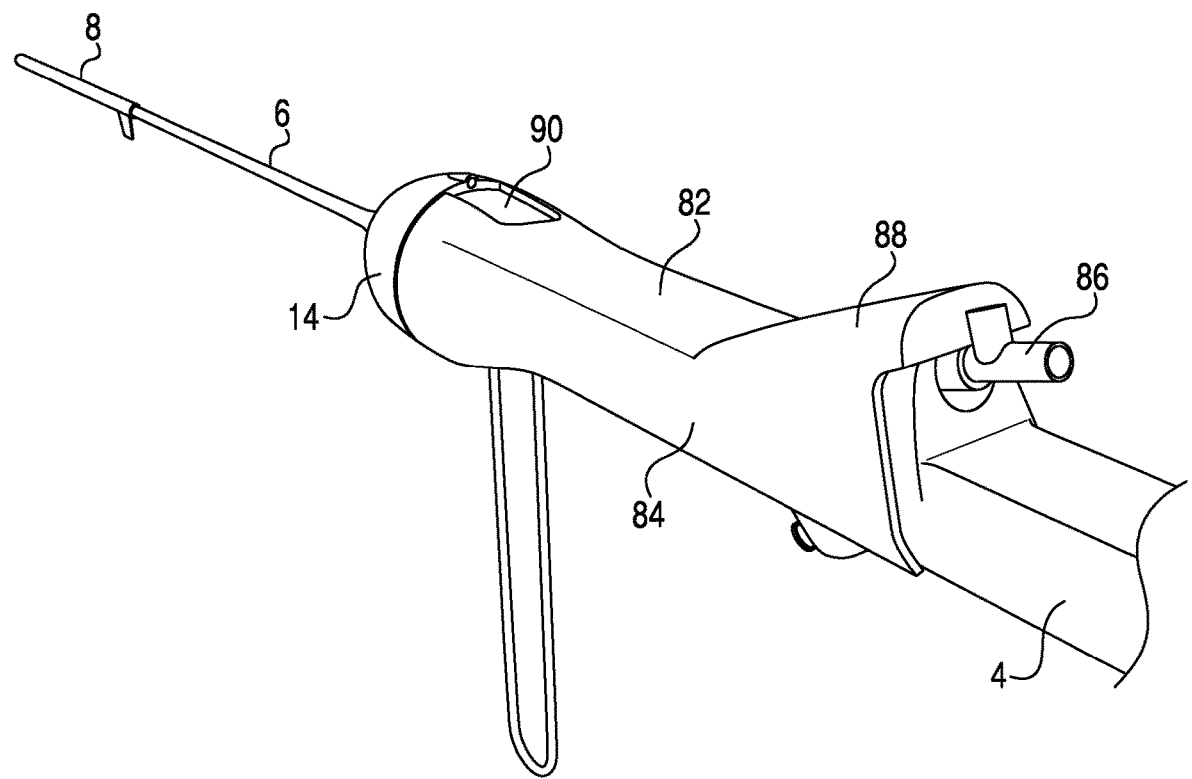
FIG. 6 illustrates an imaging device and an attachment that includes a connector, and first sheath, and a second sheath, according to a second example.
Figure 7:
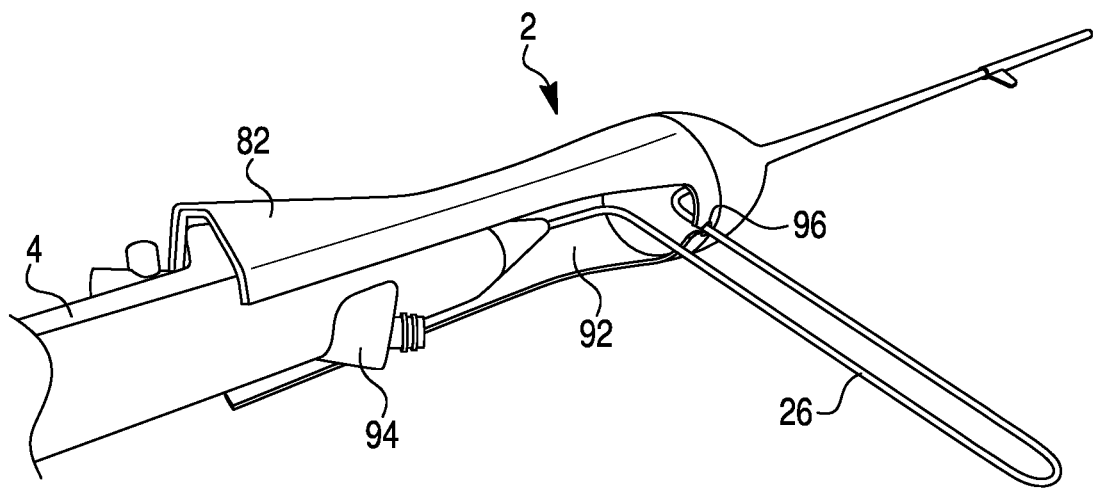
FIG. 7 illustrates a bottom perspective view of the components of FIG. 6.
Figure 8:
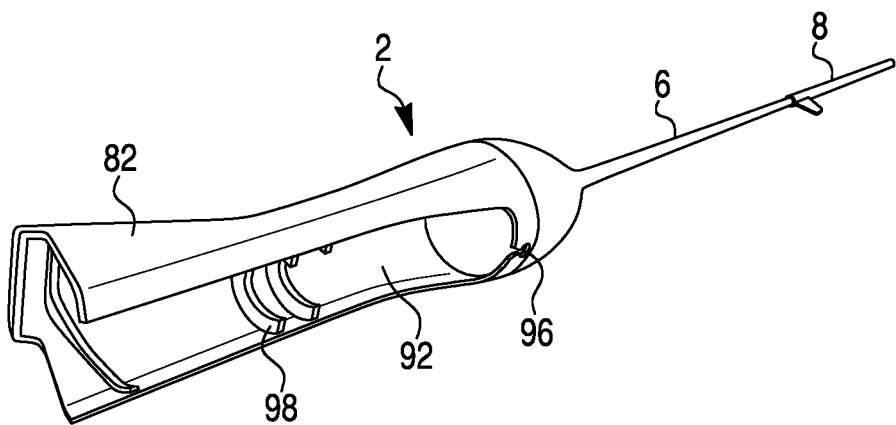
FIG. 8 illustrates a bottom perspective view of the connector, first sheath, and second sheath of FIG. 6.

FIGS. 6-8 illustrate a second aspect of a connector, referred to as connector 82. The connector 82 may be used with any of the other components previously described herein, such as the first sheath 6, the second sheath 8, and the imaging device 4. Unless otherwise specified, the connector 82 may have any feature described in connection with connector 10, including exemplary lengths, a hollow interior, interior surfaces shaped to fit around the exterior of an imaging device 4, a lip to mate with the first sheath 6, etc. In one aspect, the connector 82 may include an elongated body portion 84 that extends from the proximal portion 14 of the first sheath 6 to a region adjacent one or more ports 86 of the imaging device 4. The connector 82 may have a portion 88 that protrudes proximally and radially outward from the remaining body portion 84, creating contact with additional surfaces of the imaging device 4.

Connector 82 may include a first opening 90 in its upper wall and a second opening 92 in its lower wall. The first opening 90 may extend along a portion of the length of connector 82. The first opening 90 may facilitate insertion of a guidewire through side lumen 22 of first sheath 6 by providing space near the entry to side lumen 22. The opening 90 may also allow the user to access any underlying controls and to view the tubular member 26 and ensure that it is properly inserted into the first sheath 6, in some examples through port 40. The second opening 92 may generally extend from the proximal end to the distal end of the connector 82, as shown in FIG. 7. Similar to connector 10, near the distal end of connector 82, the second opening 92 may be connected to a smaller opening 96 configured to receive the tubular member 26 of the imaging device 4. The second opening 92 of connector 82 may include similar features and advantages as the second opening 70 of connector 10 (e.g., flexibility, space for tubular member 26) and may further provide space for other features of the imaging device 4, such as inlet 94. The opening 96 may secure the tubular member 26 with respect to the attachment 2.

Referring to FIG. 8, the connector 82 may include one or more ribs 98 to secure the connector 82 to the imaging device 4. The ribs 98 may protrude from an inner wall of the connector 82 and may extend from a first side of opening 92, around the inner wall of connector 82, to a second side of opening 92. The edge of ribs 98 may be shaped to match the contours of the handle of an imaging device 4, such as the LithoVue scope developed by Boston Scientific Corp. Therefore, when the connector 82 is placed over the handle 24 of an imaging device 4, the ribs 98 may prevent the handle 24 from rotating relative to the connector 82. Two ribs 98 may be located in a central region of the connector 82, with a third rib 98 located near a proximal end of the connector 82. However, in various aspects, the connector 82 may include one or two ribs 98 or more than three ribs, such as four, five, six, or more ribs 98.

Figure 9:
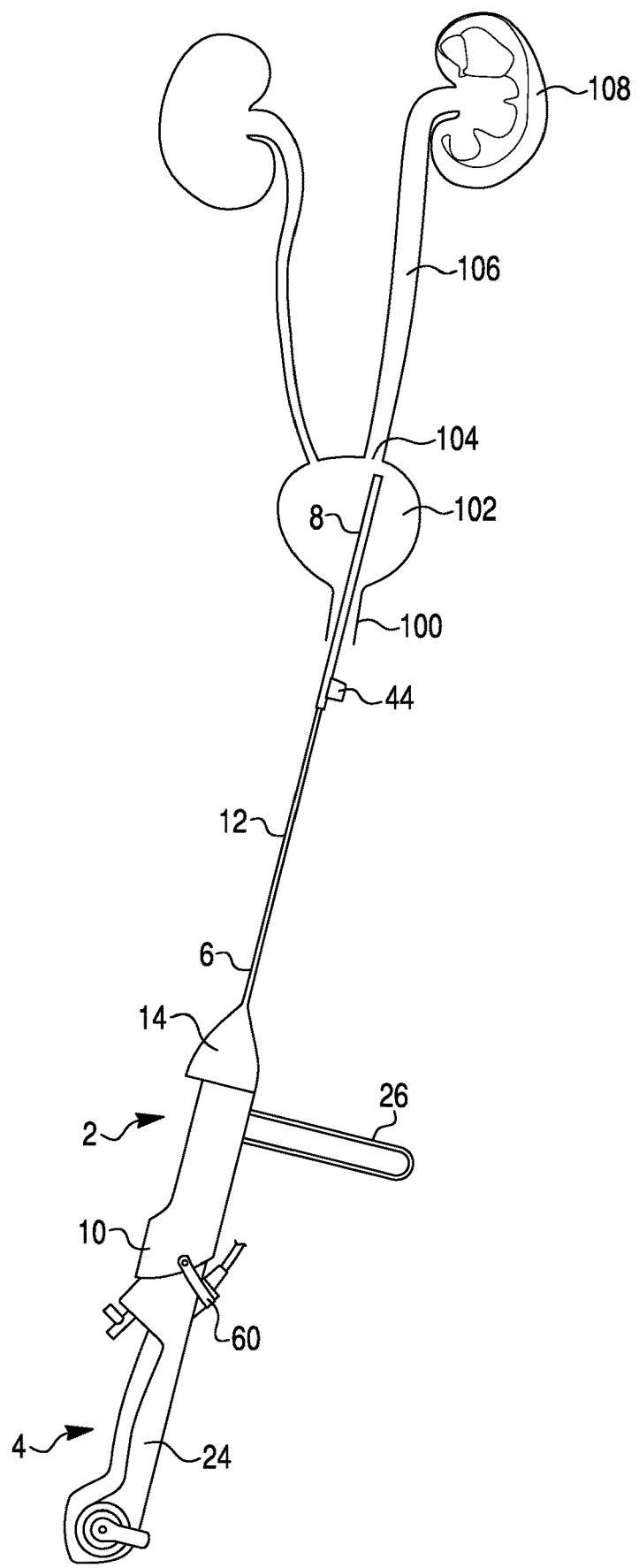
FIG. 9 illustrates a method of using an attachment according to the examples described herein.
Figure 10:
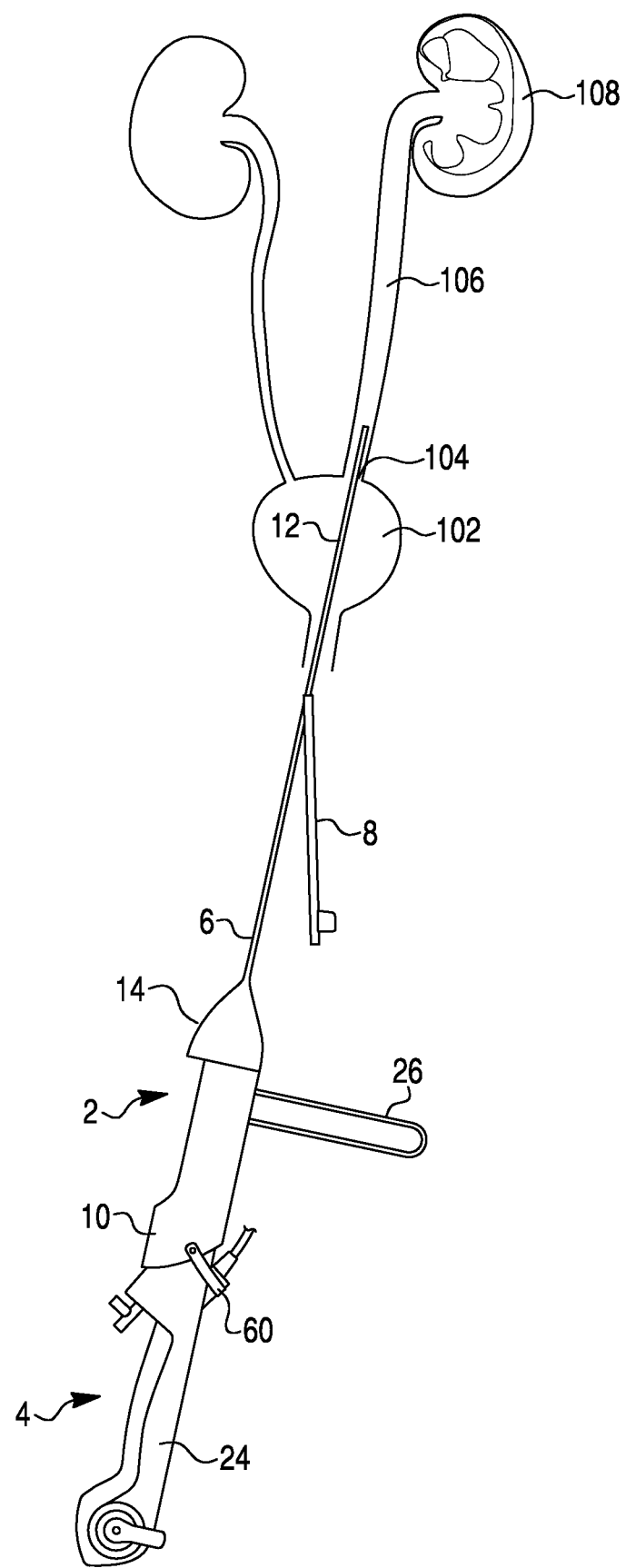
FIG. 10 illustrates removal of the second sheath from the first sheath during use.
Figure 11:
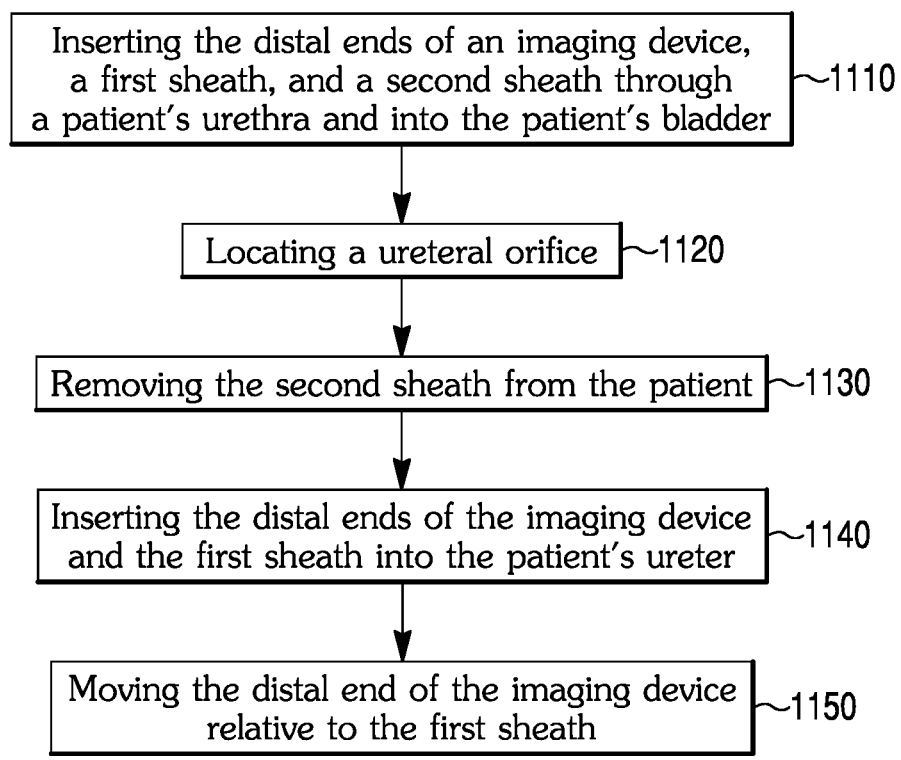
FIG. 11 illustrates a flow chart of a method for using an attachment with an imaging device.

FIGS. 9, 10, and 11 will be referenced to describe a method for using an attachment 2. The method steps may be performed with any of the components described herein (e.g., connector 10 or connector 82), although the attachment 2 of FIG. 1, with connector 10, is illustrated in the drawings and will be referenced below.

To assemble the attachment 2, the second sheath 8 may be positioned on a distal portion of the first sheath 6 by either inserting the first sheath 6 into the main lumen 46 of the second sheath 8 or by expanding the opening 56 in the wall of the second sheath 8 so that the second sheath 8 can be wrapped around the first sheath 6. The distal end of tubular member 26 may be inserted into proximal portion 14 of first sheath 6 and into the elongated shaft 12.

The user may urge the tubular member 26 through the elongated shaft 12 until the distal end of the tubular member 26 aligns with the distal end of the first sheath 6 and/or the distal end of the second sheath 8. The connector 10 may then be connected to the handle 24 of the imaging device 4 by one or both of wrapping a strap 60 around the port protrusion of the handle 24 and securing the strap 60 to the sides of connector 10, or aligning ribs 98 with the appropriate region of the handle 24 and placing the connector onto the handle 24. The tubular member 26 of the imaging device 4 may be placed within an opening 78 in the lip of the connector.

The connector 10 may be connected to the first sheath 6. The slots of the lip 34 of the first sheath 6 may be aligned with the protrusions of the lip 66 of the connector 10, and the opening 39 of the first sheath 6 may be aligned with the tubular member 26. The connector 10 and the first sheath 6 may be brought towards each other and twisted relative to each other to fully engage the protrusions with the slots, securing the connector 10 to the first sheath 6.

Once the attachment 2 is secured to the imaging device 4, the devices may be used to perform a procedure on a patient, such as a removal of a stone lodged in the ureter 106 or kidney 108. The distal ends of the second sheath 8, first sheath 6, and tubular member 26 may be inserted into the patient's urethra 100 and into the patient's bladder 102 (step 1110). The second sheath 8 may provide additional rigidity and support to the tubular member 26 and the first sheath 6 while passing through the urethra 100 and into the space within the bladder 102. The camera 28 and light 30 of the imaging device may be used to navigate through the urethra 100 and bladder 102 and to locate the ureteral orifice 104 connecting the bladder 102 to a ureter 106 (step 1120). A guidewire may be inserted through either side lumen 48 of the second sheath 8 or side lumen 22 of the first sheath 6 and into the ureter 106. In one example, two guidewires may be inserted into the ureter 106, such as a safety guidewire and a working guidewire, with one in each side lumen.

Referring to FIG. 10, the second sheath 8 may be removed from the first sheath 6. A user may grasp the grip 44 and pull the second sheath 8 proximally until the second sheath 8 is outside of the patient (step 1130). The second sheath 8 may remain around the first sheath 6 for the remainder of the procedure, or the second sheath 8 may be removed completely from the first sheath 6 via expansion of the opening 56.

The distal end of the first sheath 6, along with the distal end of the tubular member 26, may be inserted into the ureter 106 of the patient by moving the handle 24 of the imaging device 4 towards the patient (step 1140). The smaller diameter of the first sheath 6 relative to the second sheath 8 may allow it to enter the narrow pathway defined by the ureter 106. Once the shaft 12 of the first sheath 6 is in place within the patient's ureter 106, it may serve as an access sheath for the tubular member 26 or any other tools that may need to be inserted into the ureter 106 or kidney 108.

Accordingly, the connector 10 may be disconnected from the first sheath 6 and from the imaging device 4 to release the tubular member 26 and allow it to move relative to the first sheath 6. The tubular member 26 may be withdrawn from the interior of openings 78 and/or 39, and the connector 10 may be twisted relative to the first sheath 6 to release the engaged protrusions and slots. The strap 60 may be released, and the connector 10 may then be pulled away from the imaging device 4, with the handle 24 of imaging device 4 passing through the bottom opening 70. Additionally or alternatively, while leaving the connector 10 secured to one or both of the imaging device 4 or the first sheath 6, the user may reach through opening 68 in the connector 10, pull the tubular member 26 out of opening 78 of the connector 10 and opening 39 of the first sheath 6, and manipulate the tubular member 26 to either extend its distal end past the distal end of the first sheath 6 or pull its distal end proximally relative to the first sheath 6. The distal end of the tubular member 26 may then be moved relative to the first sheath 6 (step 1150)

The tubular member 26 may be used to remove stones lodged in the patient's ureter 106 or kidney 108. Various tools (e.g., lasers, baskets, etc.) may be inserted through the working lumen 32 of the tubular member 26. The tools may be used to break up stones and carry them out of the patient. When the tubular member 26 is extended from the distal end of the first sheath 6, steering control of the tubular member 26 may allow the distal end of the tubular member 26 to navigate tortuous pathways in the ureter 106 or kidney 108 and reach hard-to-access areas to break up and retrieve stones. The tools and/or the tubular member 26 may be removed from the patient one or more times through the first sheath 6. The first sheath 6 may protect the patient's urethra 100, bladder 102, and ureter 106 from damage that could be caused by passing devices into and out of the patient.

Use of the first sheath 6 and second sheath 8 to access the patient's ureter 106 eliminates the need to use a separate cystoscope to pass through the urethra 100 and bladder 102, locate the ureteral orifice 104, and place a guidewire into the patient's ureter 106 prior to inserting an access sheath and imaging device into the patient's ureter 106. Instead, the first sheath 6 and second sheath 8 are passed through the patient's urethra 100 and bladder 102 once, and the first sheath 6 is passed into the patient's ureter 106 once. All other devices are then passed through the first sheath 6. The second sheath 8 allows the use of a separate cystoscope to be eliminated by providing sufficient rigidity for the tubular member 26 and the first sheath 6 to be passed through the urethra 60 and across the bladder 62.

Figure 12:
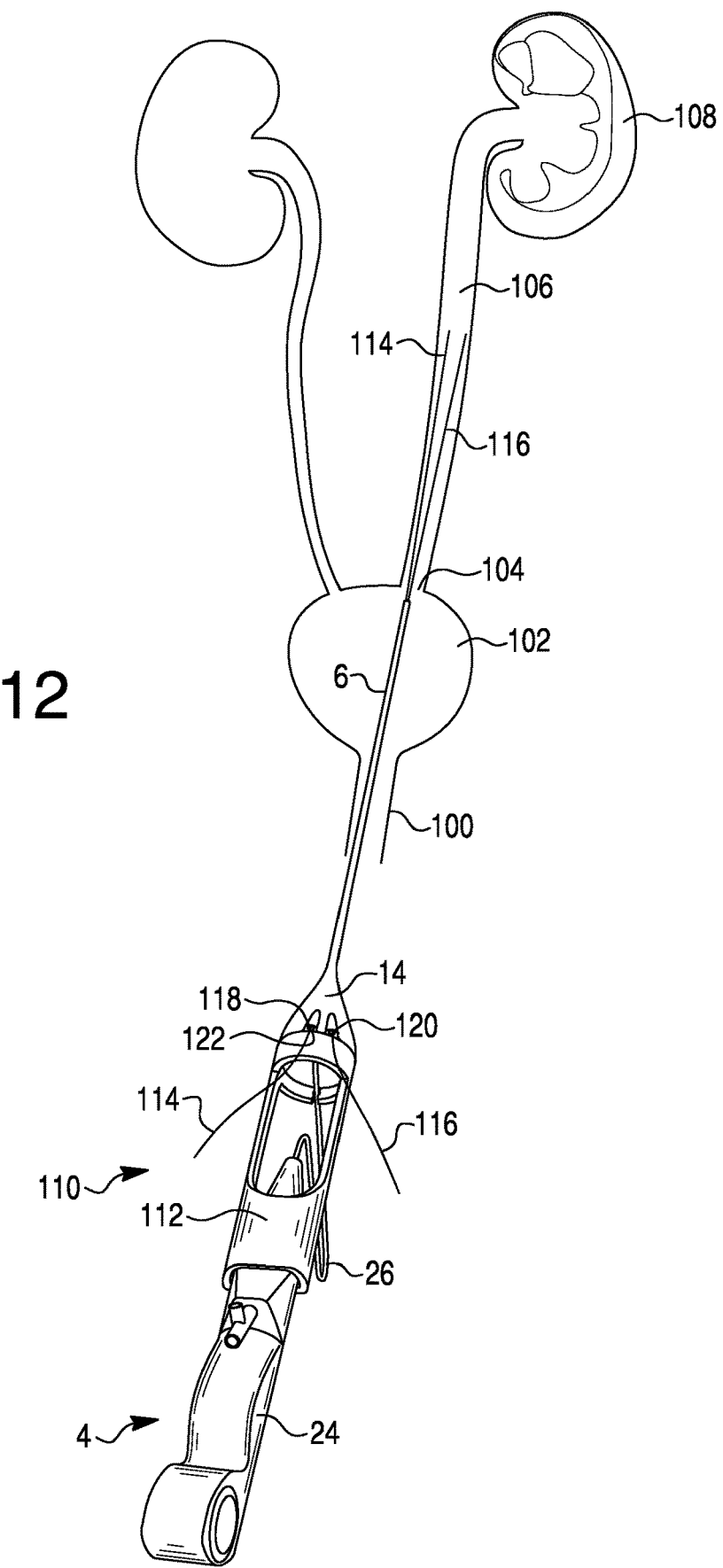
FIG. 12 illustrates a third example of a connector and a method of using the connector and the first sheath.

FIG. 12 illustrates another example of an attachment, referred to as attachment 110. Attachment 110 may include a first sheath 6, which may include any features of the first sheath 6 described in connection with other figures, and a connector 112. The first sheath 6 may include two entry ports 118, 120 configured to receive guidewires. The two entry ports 118, 120 may be a feature of any sheath 6 described herein. In one embodiment, entry port 118 may be a notch that is connected to the main interior of proximal portion 14 by an opening 122. The guidewire 114 held within entry port 118 may therefore be released from the entry port 118 so that it lies within a main lumen of the proximal portion 14. The guidewire 114 may then travel through the main lumen 20 of shaft 12 or the side lumen 22 of shaft 12.

The connector 112 may include any features described in connection with connectors 10 and 82, such as a lip to facilitate attachment to the first sheath 6, or a liner or ribs to facilitate a secure attachment to the imaging device 4. However, connector 112 may be shaped differently than connectors 10 and 82. For example, connector 112 may include a substantially cylindrical body portion. Similar to the other connectors described herein, an interior of the proximal portion of connector 112 may be contoured to fit securely around the exterior of the imaging device 4. Connector 112 may include one or more elongated openings to allow a user to reach through the openings to manipulate the tubular member 26.

In one example, the attachment 110 does not include a second sheath. With the exception of coupling a second sheath to the first sheath 6, the components of the attachment 110 may be assembled in a similar manner as described in connection with FIGS. 9 and 10. For example, the tubular member 26 may be inserted into the elongated shaft of the first sheath 6, the connector 112 may be secured to the handle 24 of the imaging device 4, and the connector 112 may be connected to the first sheath 6.

To perform a procedure on a patient, the distal end 18 of the first sheath 6 and the distal end of the tubular member 26 may be inserted through the patient's urethra 100 and into the patient's bladder 102. The camera 28 and light 30 of the imaging device 4 may be used to locate the ureteral orifice 104. The first sheath 6 may provide sufficient rigidity to support the tubular member 26 during insertion through the urethra 100 and passage across the bladder 102.

A working guidewire 114 may be inserted through an entry port 118 and a safety guidewire 116 may be inserted through an entry port 120. In one example, entry port 118 may lead to the main lumen 20 of the first sheath 6, and entry port 120 may lead to a separate side lumen 22 of the first sheath 6. The two guidewires 114, 116 may be inserted into the patient's ureter 106.

The connector 112 may be detached from the first sheath 6 and/or the imaging device 4, and the tubular member 26 may be removed from the first sheath 6. The working guidewire 114 then may be released from entry port 118 through an opening 122 between the entry port 118 and the interior of proximal portion 14, so that a proximal portion of working guidewire 114 lies within the main lumen of the interior of proximal portion 14. The distal end of the first sheath 6 may be inserted into the patient's ureter 106 over both guidewires 114, 116, such that the first sheath 6 can serve as an access sheath for the tubular member 26 and other tools used to perform a procedure within the patient's ureter 106 or kidney 108 (similar to methods described above). Accordingly, the tubular member 26 of the imaging device 4 and/or other tools may be inserted back into the first sheath 6 one or more times, as described above.

While principles of the present disclosure are described herein with reference to illustrative examples for particular applications, it should be understood that the disclosure is not limited thereto. Those having ordinary skill in the art and access to the teachings provided herein will recognize additional modifications, applications, examples, and substitution of equivalents all fall within the scope of the examples described herein. Accordingly, the invention is not to be considered as limited by the foregoing description.

We claim:

1. An attachment for an imaging device, comprising:
a first sheath;
a second sheath positioned around an exterior of the first sheath; and
a connector removably coupled to the first sheath and configured to be coupled to the imaging device, wherein the connector includes:
a body including an interior wall defining an interior configured to receive a portion of the imaging device; and
on the interior wall, at least one of (i) a liner and (ii) a rib, wherein the at least one of the liner or the rib is configured to secure the imaging device relative to the connector;
wherein the body of the connector further includes a side opening in a side wall and a distal opening, wherein the side opening is configured to receive a shaft of the imaging device such that a length of the shaft is held outside of the connector and the first sheath, and the distal opening is configured to receive a portion of the first sheath.

2. The attachment of claim 1, wherein the connector further includes a slot in the side wall, and the slot extends proximally from the side opening, wherein the slot and the side opening are each configured to receive the shaft of the imaging device.

3. The attachment of claim 1, wherein the second sheath includes a proximal end, a distal end, and an opening in a wall of the second sheath, wherein the opening extends from the proximal end of the second sheath to the distal end of the second sheath.

4. The attachment of claim 3, wherein the second sheath is configured to be (i) retracted proximally relative to the first sheath, and (ii) removable from the first sheath by being retracted proximally relative to the first sheath and/or being pulled from the first sheath via the opening of the second sheath.

5. The attachment of claim 1, wherein the second sheath has a proximal end and a distal end, and the proximal end is located distal of the proximal end of the first sheath, and distal of the connector.

6. The attachment of claim 1, wherein the second sheath is slidable axially along the first sheath.

7. The attachment of claim 1, wherein the at least one of the liner or the rib includes an edge shaped to match a contour of a handle of the imaging device.

8. The attachment of claim 1, wherein the at least one of the liner or the rib is configured to prevent a handle of the imaging device from rotating relative to the connector.

9. An attachment for an imaging device, comprising:
a first sheath including a proximal end, a distal end, and a lumen extending between the proximal end and the distal end;
a second sheath; and
a connector coupled to the first sheath, wherein the connector includes an interior configured to receive a portion of the imaging device,
wherein the second sheath is removable from the first sheath by being retracted proximally relative to the first sheath,
wherein the connector includes:
a lateral opening extending along a side wall, wherein the lateral opening is configured to receive and expose both a distal portion of a handle of the imaging device and a portion of a shaft of the imaging device, and
a plurality of ribs protruding from an interior wall of the connector.

10. The attachment of claim 9, wherein the plurality of ribs is configured to prevent the handle of the imaging device from rotating relative to the connector.

11. The attachment of claim 9, wherein the lateral opening extends proximally from a distal opening of the connector.

12. The attachment of claim 9, wherein the proximal end of the first sheath has a larger diameter than the distal end of the first sheath.

13. The attachment of claim 9, wherein the second sheath is secured to the first sheath by a friction fit, and the second sheath is removably coupled to the first sheath.

14. The attachment of claim 9, wherein the connector is removably coupled to the proximal end of the first sheath.

15. An attachment for an imaging device, comprising:
a first sheath including a proximal end, a distal end, and a lumen extending between the proximal end and the distal end;
a second sheath; and
a connector coupled to the first sheath, wherein the connector includes an interior configured to receive a portion of the imaging device,
wherein the second sheath is removable from the first sheath by being retracted proximally relative to the first sheath,
wherein the connector includes:
a lateral opening extending along a side wall, wherein the lateral opening is configured to receive both a distal portion of a handle of the imaging device and a portion of a shaft of the imaging device, and
a liner on an interior wall of the connector.

16. The attachment of claim 15, wherein the liner comprises a silicone liner.

17. The attachment of claim 15, wherein the lateral opening extends proximally from a distal opening of the connector.

18. The attachment of claim 15, wherein the second sheath is secured to the first sheath by a friction fit, and the second sheath is removably coupled to the first sheath.

* * * * *